(12) United States Patent
Mueller et al.

(10) Patent No.: US 12,123,086 B2
(45) Date of Patent: *Oct. 22, 2024

(54) METHOD FOR PRODUCING MAGNESIUM ALLOY

(71) Applicant: BIOTRONIK AG, Buelach (CH)

(72) Inventors: Heinz Mueller, Diedrichshagen (DE); Peter Uggowitzer, Ottenbach (CH); Joerg Loeffler, Greifensee (CH)

(73) Assignee: BIOTRONIK AG, Buelach (CH)

( * ) Notice: Subject to any disclaimer, the term of this patent is extended or adjusted under 35 U.S.C. 154(b) by 106 days.

This patent is subject to a terminal disclaimer.

(21) Appl. No.: 17/185,521

(22) Filed: Feb. 25, 2021

(65) Prior Publication Data

US 2021/0198778 A1 Jul. 1, 2021

Related U.S. Application Data

(62) Division of application No. 14/395,709, filed as application No. PCT/EP2013/063110 on Jun. 24, 2013, now abandoned.

(60) Provisional application No. 61/664,224, filed on Jun. 26, 2012.

(51) Int. Cl.
| | |
|---|---|
| *C22F 1/06* | (2006.01) |
| *A61F 2/82* | (2013.01) |
| *A61L 27/04* | (2006.01) |
| *A61L 27/58* | (2006.01) |
| *A61L 31/02* | (2006.01) |
| *A61L 31/14* | (2006.01) |
| *C22C 23/02* | (2006.01) |

(52) U.S. Cl.
CPC ............... *C22F 1/06* (2013.01); *A61F 2/82* (2013.01); *A61L 27/047* (2013.01); *A61L 27/58* (2013.01); *A61L 31/022* (2013.01); *A61L 31/148* (2013.01); *C22C 23/02* (2013.01)

(58) Field of Classification Search
CPC .......... A61F 2/82; A61L 27/047; A61L 27/58; A61L 31/022; A61L 31/148; C22C 23/02; C22F 1/06
USPC ...................................................... 420/405
See application file for complete search history.

(56) References Cited

U.S. PATENT DOCUMENTS

| | | | |
|---|---|---|---|
| 3,320,055 A | 5/1967 | Foerster | |
| 5,055,254 A | 10/1991 | Zuliani | |
| 5,698,158 A | 12/1997 | Lam et al. | |
| 8,518,102 B2 | 8/2013 | Kitaoka et al. | |
| 9,072,618 B2 | 7/2015 | Doerr et al. | |
| 9,561,308 B2 | 2/2017 | Schaffer | |
| 9,593,397 B2 | 3/2017 | Imwinkelried et al. | |
| 9,677,151 B2 | 6/2017 | Wegmann et al. | |
| 10,995,398 B2* | 5/2021 | Mueller | A61L 27/58 |
| 2008/0031765 A1 | 2/2008 | Gerold et al. | |
| 2009/0171452 A1 | 7/2009 | Yamamoto et al. | |
| 2010/0075162 A1 | 3/2010 | Yang et al. | |
| 2011/0054629 A1 | 3/2011 | Seok et al. | |
| 2011/0076178 A1 | 3/2011 | Somekawa et al. | |
| 2011/0192500 A1 | 8/2011 | Uggowitzer et al. | |
| 2011/0315282 A1 | 12/2011 | Somekawa et al. | |
| 2012/0035740 A1 | 2/2012 | Koo et al. | |
| 2012/0095548 A1 | 4/2012 | Gregorich et al. | |
| 2012/0128997 A1 | 5/2012 | Numano et al. | |
| 2012/0269673 A1 | 10/2012 | Koo et al. | |
| 2013/0039805 A1 | 2/2013 | Somekawa et al. | |
| 2013/0131814 A1 | 5/2013 | Koo et al. | |
| 2013/0144290 A1 | 6/2013 | Schiffl et al. | |
| 2013/0315282 A1 | 11/2013 | Mayer | |
| 2014/0065009 A1 | 3/2014 | Imwinkelried et al. | |
| 2014/0261911 A1 | 9/2014 | Imwinkelried et al. | |
| 2015/0080938 A1 | 3/2015 | Groff | |
| 2015/0080998 A1 | 3/2015 | Mueller et al. | |
| 2015/0119995 A1 | 4/2015 | Mueller et al. | |

(Continued)

FOREIGN PATENT DOCUMENTS

| | | |
|---|---|---|
| CN | 1743486 A | 3/2006 |
| CN | 1792383 | 6/2006 |

(Continued)

OTHER PUBLICATIONS

Bakhsheshi-Rad, et al., Characterization and Corrosion Behavior of Biodegradable Mg—Ca and Mg—Ca—Zn Implant Alloys, Appl. Mech. Mater, Jan. 2012, 121-126, 568-572 (Abstract Only).

Sun, Yu, et al., Preparation and Characterization of a New Biomedical Mg—Zn—Ca Alloy, Materials and Design, vol. 34, pp. 56-64, Feb. 2012 (Abstract Only).

Koike, Junichi, Dislocation Plasticity and Complementary Deformation Mechanisms in Polycrystalline Mg Alloys, Mater. Sci. Forum, Mar. 2004, 4999-452, 665-668 (Abstract Only).

Wilson, D.V., et al., Effects of Preferred Orientation on the Grain Size Dependence of Yield Strength in Metals, Philos. Mag., Jun. 1963, 1543-1551 (Abstract Only).

(Continued)

*Primary Examiner* — Jie Yang
(74) *Attorney, Agent, or Firm* — Greer, Burns & Crain, Ltd.; Steven P. Fallon

(57) ABSTRACT

A method for producing a magnesium alloy having improved mechanical and electrochemical properties. The method includes generating a high-purity magnesium by vacuum distillation. A billet of the alloy is generated by synthesis of the high-purity magnesium with 2.0 to 10.0% by weight Al, the remainder being magnesium containing impurities, which promote electrochemical potential differences and/or the formation of precipitations and/or intermetallic phases, in a total amount of no more than 0.0063% by weight of Fe, Si, Mn, Co, Ni, Cu, Zr, Y, Sc or rare earths having the ordinal numbers 21, 57 to 71 and 89 to 103, Be, Cd, In, Sn and/or Pb as well as P, wherein the matrix of the alloy includes intermetallic phases formed of Mg and Al. The alloy is homogenized by annealing at a temperature between 150° C. and 450° C. The homogenized alloy is formed in the temperature range between 200° C. and 400° C.

9 Claims, No Drawings

(56) References Cited

U.S. PATENT DOCUMENTS

| | | | |
|---|---|---|---|
| 2015/0129091 | A1 | 5/2015 | Mueller et al. |
| 2015/0129092 | A1 | 5/2015 | Mueller et al. |
| 2016/0022876 | A1 | 1/2016 | Imwinkelried et al. |

FOREIGN PATENT DOCUMENTS

| | | | |
|---|---|---|---|
| CN | 1792384 | A | 6/2006 |
| CN | 101629260 | A | 1/2010 |
| CN | 10165891 | A | 3/2010 |
| CN | 101658691 | A | 3/2010 |
| CN | 101899600 | A | 12/2010 |
| CN | 101948957 | A | 1/2011 |
| CN | 102312144 | A | 1/2012 |
| DE | 1483204 | A1 | 10/1969 |
| DE | 102006060501 | A1 | 6/2008 |
| DE | 102010027532 | A1 | 1/2012 |
| EP | 0295397 | A1 | 12/1988 |
| EP | 1959025 | A1 | 8/2008 |
| EP | 2085100 | A2 | 8/2009 |
| EP | 2384725 | A1 | 11/2011 |
| JP | 02047238 | A | 2/1990 |
| JP | 07018364 | A | 1/1995 |
| JP | H11502565 | A1 | 3/1999 |
| JP | 2007098470 | A | 4/2007 |
| JP | 2010163635 | A * | 7/2010 |
| JP | 2010529288 | A | 8/2010 |
| JP | 2012082474 | A | 4/2012 |
| RU | 1770431 | A1 | 10/1992 |
| RU | 2098506 | C1 | 12/1997 |
| RU | 2198234 | C2 | 2/2003 |
| RU | 2437949 | C1 | 12/2011 |
| SU | 557116 | A1 | 5/1977 |
| SU | 1502648 | A1 | 8/1989 |
| WO | 9626297 | A1 | 8/1996 |
| WO | 1997040201 | | 10/1997 |
| WO | 2004013364 | | 2/2004 |
| WO | 2005108634 | | 11/2005 |
| WO | 2007058276 | | 5/2007 |
| WO | 2008016150 | | 2/2008 |
| WO | 2009147861 | | 12/2009 |
| WO | 2009148093 | | 12/2009 |
| WO | 2010082669 | | 7/2010 |
| WO | 2011051424 | | 5/2011 |
| WO | 2011114931 | | 9/2011 |
| WO | 2012003522 | | 1/2012 |
| WO | 2013107644 | | 7/2013 |
| WO | 2014001321 | | 1/2014 |
| WO | 2014159328 | | 10/2014 |

OTHER PUBLICATIONS

L'Ecuyer, J.D., et al., Precipitation Interactions with Dynamic Recrystallization of HSLS Steel, Acta Metallurigica, Apr. 1989, 37, 4, 1023-1031 (Abstract Only).
International Search Report for PCT/US2014/023047, Jan. 31, 2014.
International Search Report for PCT/US2013/057294, Jun. 17, 2014.
Xu, Bingshe, et al., 1200 Questions on Nonferrous Metallurgy; 747, How to Prepare Highly Pure Magnesium, Jan. 1, 2008.
ASTM International, Standard Specification for Magnesium-Alloy Die Castings, 1998.
European Committee for Standardization, Magnesium and Magnesium Alloys, 1998.
Kannan et al., "Evaluating the stress corrosion cracking susceptibility of Mg—Al—Zn alloy in modified-simulated body fluid for orthopaedic implant application", Scripta Materialia, 59 (2008) 175-178.
Kammer, Catrin, et al., "Magnesium Taschenbuch", Aluminium-Verlag, Duesseldorf (2000), pp. 156-161.
Li Xuesong, et al., "Microstructure, mechanical properties and corrosion behavior of Mg—1Zn—0.5Ca alloy", Advanced Materials Research, Trans Tech Publications Ltd., vol. 311-313, Jan. 1, 2011, pp. 1735-1740.
Martienssen, Werner, et al, "Springer Handbook of Condensed Matter and Materials Data—Part 3.1 ", Springer-Verlag Berlin Heidelberg, New York, (2005), pp. 160-170 and cover pages (23 pages).
Oh, J.C., et al., "TEM and 3DAP characterization of an age-hardened Mg—Ca—Zn alloy", Scripta Materialia, vol. 53, No. 6, Sep. 1, 2005, pp. 675-679.
Oh-Ishi, K., et al., "Influence of Zn additions on age hardening response and microstructure of Mg-0.3at.% Ca alloys", Magnesium Technology 2010, "Proceedings of a Symposium Held During [the] TMS Annual Meeting & Exhibition," Jan. 1, 2010, pp. 517-520.
Oh-Ishi, K., et al., "Age-hardening response of Mg-0.3 at. %Ca alloys with different Zn contents," Materials Science and Engineering, A: vol. 526, Nos. 1-2, Nov. 25, 2009, pp. 177-184.
Radeck, Stephanie, "International Search Report and Written Opinion of the International Searching Authority", Patent Cooperation Treaty Application PCT/EP2013/063253, European Patent Office as International Search Authority, Search Completed Sep. 26, 2013, International Search Report Mailed Oct. 4, 2013, 13 pages.
Schuetze, Michael, et al., "Fundamentals of High Temperature Corrosion", Materials Science and Technology, Wiley-VCH Verlag GmbH, 2000, pp. 67-129.
Somekawa, H., et al., "High strength and fracture toughness balance on the extruded Mg—Ca—Zn alloy", Materials Science and Engineering: A, vol. 459, Nos. 1-2, Jun. 25, 2007, pp. 366-370.
Song, G., et al., "Corrosion of Non-Ferrous Alloys. III. Magnesium Alloys", Materials Science and Technology, Wiley-VCH Verlag GmbH, 2000, pp. 131-171.
Yang, M.B., et al., "Comparison of as-cast microstructures and solidification behaviours of Mg—Zn—Al ternary magnesium alloys with different Zn/Al mass ratios," Advanced Materials Research , Trans Tech Publications Ltd., vol. 548, Jan. 1, 2012, pp. 321-327.
Zhang, B.P., et al., "Enhanced mechanical properties in fine-grained Mg—1.0Zn—0.5Ca alloys prepared by extrusion at different temperatures", Scripta Materialia, vol. 63, No. 10, Nov. 1, 2010, pp. 1024-1027.
European Office Action, European Application 13 730 893.8, Dated Apr. 19, 2017.
Russian Office Action, 2015101291/02, dated Jun. 2, 2017.
Japanese Office Action, 2015-518992, dated Jun. 1, 2017.
Zou, Hong-hui, "Effects of microstructure on creep behavior of Mg-5%Zn-2%(-2%YY) alloy", Trans. Nonferrous Met. Soc. China, vol. 18, (2008), pp. 580-587.
International Search Report, WO/2014/001241, dated Feb. 12, 2013.
Russian Office Action, 2015102168/02, dated Jun. 2, 2017.
European Office Action, European Application 13 729 770.1, Dated Apr. 19, 2017.
European Office Action, European Application 13 730 613.0, Dated Apr. 19, 2017.
Japanese Office Action, 2015-519055, dated Jun. 1, 2017.
Chinese Office Action, 201380022712.7, dated Feb. 29, 2016.
Chinese Office Action, 201380022712.7, dated Nov. 18, 2016.
Chinese Office Action, 201380022712.7, dated May 25, 2017.
Wenjiang, Ding et al. Science and Technology of Magnesium Alloys, Science Publishing House, Jan. 2007, p. 323-324.
Russian Office Action, 2015102166/02, dated Jun. 1, 2017.
Sun, Yu, et al., "Preparation and characterization of a new biomedical MgZnCa alloy", Materials and Design, vol. 34, Jul. 23, 2011, pp. 58-64.
European Office Action, European Application 13 731 134.6, Dated Apr. 19, 2017.
Xie, Yang, State Intellectual Property Office of the People's Republic of China Notification of the First Office Action, Application No. 201380022716.5, Issued Mar. 3, 2016, 11 pages.
Hillis, et al., "Compositional Requirements for Quality Performance with High Purity", International Magnesium Association Meeting; 55th, International Magnesium Association, (1998), pp. 74-81.
Geis-Gerstorfer, J., et al., "Blood triggered corrosion of magnesium alloys", Materials Science and Engineering B, 176, (2011), pp. 1761-1766.

(56) References Cited

OTHER PUBLICATIONS

He, Youlian, et al., "Production of Very Fine Grained Mg-3%Al-1%Zn Alloy by Continuous Extrusion Forming (CONFORM)", Advanced Engineering Materials, 12, No. 9, (2010), pp. 843-847.
Jin, Li, et al., "Mechanical properties and microstructure of AZ31 Mg alloy processed by two-step equal channel angular extrusion", Materials Letters, 59, (2005), pp. 2267-2270.
Wang, Xi-Shu, et al., "Effect of equal channel angular extrusion process on deformation behaviors of Mg—3Al—Zn alloy", Materials Letters, 62, (2008), pp. 1856-1858.
Chinese Office Action Dated Feb. 1, 2016.
International Search Report Dated Jan. 30, 2014.
Kakutani et al., "Filiform Corrosion of a High Purity AZ31 Magnesium Alloy", Journal of the Japan Institute of Metals, 2008, pp. 420-426, vol. 72, No. 6, The Japan Institute of Metals.
European Search Report from the corresponding European Patent Application No. 21167104, dated Aug. 27, 2021.
Hanawalt, et al., Corrosion Studies of Magnesium and Its Alloys, Metals Technology, Sep. 1941, 273-299.
Li, Wen, et al., Preparation and in Vitro Degradation of the Composite Coating with High Adhesion Strength on Biodegradable Mg—Zn, Ca Alloy, Materials Characterization 62 (2011), 1158-1165.
Cha, Pil-Ryung, et al., Biodegradability Engineering of Biodegradable Mg Alloys: Tailoring the Electrochemical Properties and Microstructure of Constituent Phases, Scientific Reports 3:2367, 1-6, 2013.
Song, Yingwei, et al., The Role of Second Phases in the Corrosion Behavior of Mg—5Zn Alloy, Corrosion Science 60 (2012) 238-245.
Abidin, Nor Ishida Zainal, et al., Corrosion of High Purity Mg, Mg2Zn0.2Mn,ZE41 and AZ91 in Hank's Solution at 37° C., Corrosion Science 53 (2011) 3542-3556.
Bakhsheshi-Rad, H.R., et al., Relationship Between the Corrosion Behavior and the Thermal Characteristics and Microstructure of Mg—0.5Ca—xZn Alloys, Corrosion Science 64 (2012) 184-197.
Sugiura, Tsutomu, et al., A Comparative Evaluation of Osteosynthesis with Lag Screws, Miniplates, or Kirschner Wires for Mandibular Condylar Process Fractures, J. Oral Maxillofac Surg 59:1161-1168, 2001.
Manohar, P.A., et al., Five Decades of the Zenar Equation, ISIJ International, vol. 38 (1998), No. 9, pp. 913-924.
Wang, Bin, et al., Biocorrosion of Coated Mg—Zn—Ca Alloy under Constant Compressive Stress Close to that of Human Tibia, Materials Letters 70 (2012) 174-176.
Barnett, M.R., et al., Influence of Grain Size on the Compressive Deformation of Wrought Mg—3Al—1Zn, Acta Materiala 52 (2004) 5093-5103.
Du, Hui, et al., Effects of Zn on the Microstructure, Mechanical Property and Bio-Corrosion Property of Mg—3CA Alloys for Biomedical Application, Materials Chemistry and Physics 125 (2011) 568-575.
Kirkland, Nicholas, et al., In Vitro Dissolution of Magnesium-Calcium Binary Alloys: Clarifying the Unique Role of Calcium Additions in Bioresorbable Magnesium Implant Alloys, Wiley Online Library, 2010, 91-100.
Zhang, Erlin, et al., Microstructure, Mechanical Properties and Bio-Corrosion Properties of Mg—Zn—Mn—Ca Alloy for Biomedical Application, Materials Science and Engineering A 497 (2008) 111-118.
Song, Guang Ling, et al., Understanding Magnesium Corrosion, A Framework for Improved Alloy Performance, Advanced Engineering Materials, 2003, 5, No. 12, 837-858.
Song, Guang Ling, et al., Corrosion Mechanisms of Magnesium Alloys, Advanced Engineering Materials, 1999, 1, No. 1, 11-33.
Abidin, Nor Ishida Zainal et a . . . , The In Vivo and in Vitro Corrosion of High-Purity Magnesium and Magnesium Alloys WZ21 and AZ91, Corrosion Science 75 (2013) 354-366.
Kirkland, N.T., et al., Assessing the Corrosion of Biodegradable Magnesium Implants: A Critical Review of Current Methodologies and Their Limitations, Acta Biomaterialia 8 (2012) 925-936.
Kirkland, Nicholas T., et al., Buffer-Regulated Biocorrosion of Pure Magnesium, J. Mater Sci: Mater Med. (2012) 23: 283-291.
Hanzi, Anja C., et al., On the In Vitro and In Vivo Degradation Performance and Biological Response of New Biodegradable Mg—Y—Zn Alloys, Acta Biomateriala 6 (2010) 1824-1833.
Yamamoto, Akiko, et al., Effect of Inorganic Salts, Amino Acids and Proteins on the Degradation of Pure Magnesium in Vitro, Materials Science and Engineering C 29 (2009) 1559-1568.
Cao, Fuyong, et al., Corrosion of Ultra-High-Purity Mg in 3.5% NaCl Solution Saturated with Mg(OH)2, Corrosion Science 75 (2013) 78-99.
Kalb, H., et al., Impact of Microgalvanic Corrosion on the Degradation Morphology of WE43 and Pure Magnesium under Exposure to Simulated Body Fluid, Corrosion Science 57 (2012) 122-130.
Schinhammer, Michael, et al., On the Immersion Testing of Degradable Implant Materials in Simulated Body Fluid: Active pH Regulation Using CO2, Advanced Engineering Materials, 2013, 15, No. 6, 434-441.
Liu, Ming, et al., Calculated Phase Diagrams and the Corrosion of Die-Cast Mg—Al Alloys, Corrosion Science, 2009, 602-619.
Pilcher, Karin, et al., Immunological Response to Biodegradable Magnesium Implants, JOM, vol. 66, No. 4, 2014.
Kraus, Tanja, et al., Magnesium Alloys for Temporary Implants in Osteosynthesis: In Vivo Studies of their Degradation and Interaction with Bone, Acta Biomaterialia 8 (2012) 1230-1238.
Homma, T., et al., Effect of Zr Addition on the Mechanical Properties of As-Extruded Mg—Zn—Ca—Zr Alloys, Materials Science and Engineering A 527 (2010) 2356-2362.
Mendis, C.L., et al., Precipitation-Hardenable Mg—2.4Zn—0.1Ag—0.1Ca—0.16Zr (at.%) Wrought Magnesium Alloy, Acta Materialia 57 (2009) 749-760.
Koike, J., et al., The Activity of Non-Basal Slip Systems and Dynamic Recovery at Room Temperature in Fine-Grained AZ31B Magnesium Alloys, Acta Materialia 51 (2003) 2055-2065.
Hanzi, A.C., et al., Design Strategy for Microalloyed Ultra-Ductile Magnesium Alloys, Philosophical Magazine Letters, vol. 89, No. 6, Jun. 2009, 377-390.
Bamberger, M., et al., Trends in the Development of New Mg Alloys, Annu. Rev. Mater. Res. 2008, 38:505-33.
Farahany, Saeed, et al., In-Situ Thermal Analysis and Macroscopical Characterization of Mg—xCA and Mg—0.5Ca—xZn Alloy Systems, Thermochimica Acta 527 (2012) 180-189.
Zhang, Baoping, et al., Mechanical Properties, Degradation Performance and Cytotoxicity of Mg—Zn—Ca Biomedical Alloys with Different Compositions, Materials Science and Engineering C 31 (2011) 1667-1673.
Gunde, P., et al., High-Strength Magnesium Alloys for Degradable Implant Applications, Materials Science and Engineering, A 528 (2011) 1047-1054.
Stefanidou, M. et al., Zinc: A Multipurpose Trace Element, Arch Toxicol (2006) 80: 1-9.
Tapiero, Haim, et al., Trace Elements in Human Physiology and Pathology: Zinc and Metallothioneins, Biomedicine & Pharmacotherapy 57 (2003) 399-411.
Hanzi, A.C., et al., Design Considerations for Achieving Simultaneously High-Strength and Highly Ductile Magnesium Alloys, Philosophical Magazine Letters 2012, 1-11.
Zberg, Bruno, et al., MgZnCa Glasses Without Clinically Observable Hydrogen Evolution for Biodegradable Implants, Nature Materials, vol. 8, Nov. 2009, 887-891.
Staiger, Mark P., et al., Magnesium and its Alloys as Orthopedic Biomaterials: A Review, Biomaterials 27 (2006) 1728-1734.
Witte, Frank, et al., Degradable Biomaterials Based on Magnesium Corrosions, Current Opinion in Solid State and Materials Science (2009).
Zhang, Shaoxiang, et al., Research on an Mg—Zn Alloy as Degradable Biomaterial, Acta Biomaterialia 6 (2010) 626-640.
Song, Guangling, Control of Biodegradation of Biocompatible Magnesium Alloys, Corrosion Science 49 (2007) 1696-1701.
Hofstetter, J., et al., High-Strength Low-Alloy (HSLA) Mg—Zn—Ca Alloys with Excellent Biodegradation Performance, JOM, vol. 66, No. 4, 2014.

(56) References Cited

OTHER PUBLICATIONS

Mendis, C.L., et al., An Enhanced Age Hardening Response in Mg—Sn Based Alloys Containing Zn, Materials Science and Engineering A 435-436 (2006) 163-171.
Sudholz, A.D., et al., Corrosion Behaviour of Mg-Alloy AZ91E with Atypical Alloying Additions, Journal of Alloys and Compounds 471 (2009) 109-115.
Chia, T.L., et al., The Effect of Alloy Composition on the Microstructure and Tensile Properties of Binary Mg-rare Earth Alloys, Intermetallics 17 (2009) 481-490.
Birbilis, N., et al., On the Corrosion of Binary Magnesium-Rare Earth Alloys, Corrosion Science 51 (2009) 683-689.
Birbilis, N., et al., A Combined Neural Network and Mechanistic Approach for the Prediction of Corrosion Rate and Yield Strength of Magnesium-Rare Earth Alloys, Corrosion Science 53 (2011) 168-176.
A.D. Sudholz, et al., Electrochemical Properties of Intermetallic Phases and Common Impurity Elements in Magnesium Alloys, Electrochemical and Solid-State Letters, 14 (2) C5-C7 (2011).
Shaw, Barbara, Corrosion Resistance of Magnesium Alloys, ASM Handbook, vol. 13A, 2003,692-696.

\* cited by examiner

METHOD FOR PRODUCING MAGNESIUM ALLOY

PRIORITY CLAIM

This application is a divisional of and claims priority under 35 U.S.C. §§ 120 and 121 from prior pending U.S. application Ser. No. 14/395,709, which was filed on Oct. 20, 2014, which was a U.S. National Phase under 35 U.S.C. § 371 of International Application No. PCT/EP2013/063110, filed Jun. 24, 2013, which claims priority to U.S. Provisional Application No. 61/664,224, filed Jun. 26, 2012. The applications in this paragraph are incorporated by reference herein.

FIELD OF THE INVENTION

The invention concerns magnesium alloy materials and their use in medical implants such as stents for the treatment of diseases. Such stents provide a supporting function in hollow organs of a patient, and biocorrodible magnesium alloys must provide controlled degradation and also have strong mechanical properties and be biocompatible.

BACKGROUND

The implantation of stents has become established as one of the most effective therapeutic measures for the treatment of vascular diseases. Stents have the purpose of assuming a supporting function in hollow organs of a patient. For this purpose, stents featuring conventional designs have a filigree supporting structure comprising metal struts, which is initially present in compressed form for introduction into the body and is expanded at the site of the application. One of the main application areas of such stents is to permanently or temporarily widen and hold open vascular constrictions, particularly constrictions (stenosis) of coronary blood vessels. In addition, aneurysm stents are known, which are used primarily to seal the aneurysm. The support function is additionally provided by such aneurysm stents.

A stent has a base body made of an implant material. An implant material is a non-living material, which is employed for applications in medicine and interacts with biological systems. A basic prerequisite for the use of a material as an implant material, which is in contact with the body environment when used as intended, is biocompatibility. For the purpose of the present application, biocompatibility shall be understood to mean the ability of a material to induce an appropriate tissue reaction in a specific application. This includes an adaptation of the chemical, physical, biological, and morphological surface properties of an implant to the recipient's tissue with the aim of a clinically desired interaction. The biocompatibility of the implant material is also dependent on the temporal process of the reaction of the biosystem in which it is implanted. For example, irritations and inflammations occur in a relatively short time, which can lead to tissue changes. Depending on the properties of the implant material, biological systems thus react in different ways. According to the reaction of the biosystem, the implant materials can be divided into bioactive, bioinert and degradable or resorbable materials.

Conventional implant materials include polymers, metallic materials, and ceramic materials (as coatings, for example). Biocompatible metals and metal alloys for permanent implants include, for example, stainless steels (such as 316L), cobalt-based alloys (such as CoCrMo cast alloys, CoCrMo forge alloys, CoCrWNi forge alloys and CoCrNiMo forge alloys), pure titanium and titanium alloys (such as cp titanium, TiAl6V4 or TiAl6Nb7) and gold alloys. In the field of biocorrodible stents, the use of magnesium or pure iron as well as biocorrodible base alloys of the elements magnesium, iron, zinc, molybdenum, and tungsten have been proposed.

The use of biocorrodible magnesium alloys for temporary implants having filigree structures is made difficult in particular because degradation of the implant progresses very quickly in vivo. So as to reduce the corrosion rate, i.e., the degradation speed, different approaches are being discussed in the art. Modified alloys and coatings represent categories of approaches to reduce the corrosion rate of magnesium alloys. Some of the existing approaches show promise, but none of them has so far led to a commercially available product to the knowledge of the inventors. Regardless of the efforts made so far, there remains a need for solutions to at least temporarily reduce the corrosion of magnesium alloys in vivo, while optimizing the mechanical properties thereof at the same time.

Magnesium alloy properties are determined by the type and quantity of the alloying elements and impurities as well as the production conditions. The effects of the alloying elements and impurities on the properties of the magnesium alloys have been known to artisans. However, determining the properties of binary or ternary magnesium alloys for use as implant materials remains complex.

The alloying element used most frequently for magnesium is aluminum. Aluminum provides increased tensile strength due to solid solution and precipitation hardening and fine grain formation, but also in microporosity. Moreover, in the melt aluminum shifts the iron precipitation boundary toward drastically lower iron contents at which the iron particles precipitate or form intermetallic particles together with other elements.

Calcium exhibits a pronounced grain refining effect and worsens the castability and corrosion resistance.

Undesirable accompanying elements in magnesium alloys include iron, nickel, cobalt and copper, which cause a considerable increase in the corrosion tendency due to the electropositive nature thereof.

Manganese can be found in all magnesium casting alloys and binds iron in the form of AlMnFe precipitations, whereby the formation of local elements is reduced. On the other hand, manganese is not able to bind all the iron, and therefore a remainder of iron and a remainder of manganese are always left in the melt.

Silicon lowers the castability and viscosity, and as the content of Si rises, a worsened corrosion behavior is to be expected. Iron, manganese and silicon have a very high tendency to form an intermetallic phase. The electrochemical potential of this phase is very high and can thus act as a cathode controlling the corrosion of the alloy matrix.

As a result of solid solution hardening, zinc improves the mechanical properties and results in grain refining, however it also leads to microporosity with a tendency toward hot cracking starting at a content of 1.5 to 2% by weight in binary Mg—Zn and ternary Mg—Al—Zn alloys.

Alloying additions made of zirconium increase the tensile strength without lowering the expansion and lead to grain refining, but also to a strong impairment of dynamic recrystallization, which is manifested in an increase of the recrystallization temperature and therefore requires high energy expenditure. Moreover, zirconium cannot be added to melts containing aluminum and silicon because the grain refining effect is lost.

Rare earths such as Lu, Er, Ho, Th, Sc and In all exhibit a similar chemical behavior and form eutectic systems with partial solubility on the magnesium-rich side of the binary phase diagrams such that precipitation hardening is possible.

The addition of further alloying elements, in conjunction with the impurities, is known to cause the formation of different intermetallic phases in binary magnesium alloys. For example, the intermetallic phase $Mg_{17}Al_{12}$ forming at the grain boundaries is brittle and limits the ductility. As compared to the magnesium matrix, this intermetallic phase is more noble and able to form local elements, whereby the corrosion behavior worsens.

In addition to these influencing factors, the properties of the magnesium alloys also decisively depend on the metallurgical production conditions. Conventional casting methods automatically introduce impurities when adding, by alloying, the alloying elements. The prior art (U.S. Pat. No. 5,055,254 A) therefore defines tolerance limits for impurities in magnesium casting alloys, which, for example for a magnesium-aluminum-zinc alloy containing approximately 8 to 9.5% by weight Al and 0.45 to 0.9% by weight Zn, mentions tolerance limits of 0.0015 to 0.0024% by weight Fe, 0.0010% by weight Ni, 0.0010 to 0.0024% by weight Cu and no less than 0.15 to 0.5% by weight Mn.

Tolerance limits for impurities in magnesium and the alloys thereof as well as the production conditions are mentioned in many known documents and listed as follows in % by weight:

| Alloy | Production | State | Fe | Fe/Mn | Ni | Cu |
|---|---|---|---|---|---|---|
| Pure Mg | no information | | 0.017 | | 0.005 | 0.01 |
| AZ 91 | Die casting | F | | 0.032 | 0.005 | 0.040 |
| | High-pressure die casting | | | 0.032 | 0.005 | 0.040 |
| | Low-pressure die casting | | | 0.032 | 0.001 | 0.040 |
| | | T4 | | 0.035 | 0.001 | 0.010 |
| | | T6 | | 0.046 | 0.001 | 0.040 |
| | Gravity die casting | F | | 0.032 | 0.001 | 0.040 |
| AM60 | Die casting | F | | 0.021 | 0.003 | 0.010 |
| AM50 | Die casting | F | | 0.015 | 0.003 | 0.010 |
| AS41 | Die casting | F | | 0.010 | 0.004 | 0.020 |
| AE42 | Die casting | F | | 0.020 | 0.020 | 0.100 |

It has been found that these tolerance definitions are not sufficient to reliably exclude the formation of corrosion-promoting intermetallic phases, which in terms of electrochemistry have a more noble potential than the magnesium matrix.

Biodegradable implants, including stents, require a load-bearing function and consequently strength, together with sufficient expandability, during the physiologically necessary support periods thereof. Known magnesium materials fall far short of the strength properties provided by permanent implants made from other materials such as titanium, CoCr alloys and titanium alloys. The ultimate tensile strength $R_m$ for permanent implants is approximately 500 MPa to >1000 MPa, while that of magnesium materials is <275 MPa so far, and in most cases <250 MPa.

Another drawback of many prior magnesium materials for use in stents is that the difference between ultimate tensile strength $R_m$ and proof stress $R_p$ is small. In the case of implants that allow plastic deformation, such as cardiovascular stents, this means that no further resistance exists against deformation after initial deformation of the material, and the regions that have already been deformed are deformed further without any load increase. This can lead to overstretching of parts of the component and fracture may occur.

Many magnesium materials additionally exhibit a clearly pronounced mechanical asymmetry, which is manifested in the difference in the mechanical properties, especially the proof stress $R_p$ with tension load and compression load. Such asymmetries are created, for example, during forming processes such as extrusion, rolling and drawing, which are used to produce suitable semi-finished products. A difference between the proof stress $R_p$ during tension and the proof stress $R_p$ during compression that is too large may result in inhomogeneous deformation of a component, such as a cardiovascular stent, which later undergoes multiaxial deformation, and may cause cracking and fracture.

Because of the low number of crystallographic slip systems, magnesium alloys can generally also form textures during forming processes such as extrusion, rolling and drawing used to produce suitable semifinished products by orienting the grains during the forming process. Specifically, this means that the semifinished product has different properties in different directions in space. For example, high deformability or elongation at fracture occurs in one direction in space after forming, and reduced deformability or elongation at fracture occurs in another direction in space. The formation of such textures should likewise be avoided, because a stent is subjected to high plastic deformation, and reduced elongation at fracture increases the risk of failure of the implant. One method for substantially avoiding such textures during forming is to adjust as fine a grain as possible prior to forming. Because of the hexagonal lattice structure of magnesium materials, the ability of these materials to deform at room temperature is low, which is characterized by slip in the base plane. If the material additionally has a coarse microstructure, i.e., a coarse grain, so-called twinning is forcibly produced upon further deformation, at which shear strain occurs, which transforms a crystal region into a position that is mirror symmetrical to the starting position. The resulting twin grain boundaries constitute weak points in the material, where incipient cracking starts, especially with plastic deformation, which ultimately leads to the destruction of the component.

If the grain of the implant materials is sufficiently fine, the risk of such implant failure is drastically reduced. Implant materials should therefore have as fine a grain as possible so as to prevent such undesirable shear strain.

All available magnesium materials for implants are subject to high corrosion in physiological media. Attempts have been made to curb the corrosion tendency by providing the implants with a corrosion-inhibiting coating, for example made of polymeric materials (EP 2 085 100 A2, EP 2 384 725 A1), an aqueous or alcoholic conversion solution (DE 10 2006 060 501 A1) or an oxide (DE 10 2010 027 532 A1, EP 0 295 397 A1).

The polymeric passivation layers are controversial, because virtually all appropriate polymers also cause strong inflammations in the tissue at times. On the other hand, thin magnesium alloy structures without such protective measures do not resist corrosions for the required support periods. The corrosion on thin-walled traumatological implants is often times accompanied by an excessively fast loss of tensile strength, which poses an additional burden by forming excessive amounts of hydrogen per unit of time. The consequences are undesirable gas inclusions in the bones and tissue. In the case of traumatological implants having larger cross-sections, there is a need to be able to deliberately control the hydrogen problem and the corrosion rate of the implant by way of the structure thereof.

Specifically with biodegradable implants, there is a desire for maximum biocompatibility of the elements, because all the chemical elements that are contained are absorbed by the body after decomposition. In any case, highly toxic elements such as Be, Cd, Pb, Cr and the like should be avoided.

Degradable magnesium alloys are especially suitable for implementing implants. Stents are used, for example, to support vessels, hollow organs and vein systems (endovascular implants, such as stents).

SUMMARY OF THE INVENTION

A preferred embodiment is a method for producing a magnesium alloy having improved mechanical and electrochemical properties. The method includes generating a high-purity magnesium by vacuum distillation. A billet of the alloy is generated by synthesis of the high-purity magnesium with 2.0 to 10.0% by weight Al, the remainder being magnesium containing impurities, which promote electrochemical potential differences and/or the formation of precipitations and/or intermetallic phases, in a total amount of no more than 0.0063% by weight of Fe, Si, Mn, Co, Ni, Cu, Zr, Y, Sc or rare earths having the ordinal numbers 21, 57 to 71 and 89 to 103, Be, Cd, In, Sn and/or Pb as well as P, wherein the matrix of the alloy includes intermetallic phases formed of Mg and Al. The alloy is homogenized by annealing at a temperature between 150° C. and 450° C. The homogenized alloy is formed in the temperature range between 200° C. and 400° C. Preferably, the annealing is conducted with a holding period of at least 3 hours or between 4 to 40 hours. Preferably, the annealing is conducted with a holding period sufficient to produce a homogeneous fine grain of <10 μm. In one variation, the matrix of the alloy includes solid solutions between aluminum and zinc. In one variation, the synthesis of the high-purity magnesium is with less or equal 1.0% by weight Zn.

DETAILED DESCRIPTION OF THE PREFERRED EMBODIMENTS

A preferred embodiment provides a method for producing a magnesium alloy having improved mechanical and electrochemical properties. The method includes generating a high-purity magnesium by vacuum distillation. A billet of the alloy is generated by synthesis of the high-purity magnesium with 2.0 to 10.0% by weight Al, the remainder being magnesium containing impurities, which promote electrochemical potential differences and/or the formation of precipitations and/or intermetallic phases, in a total amount of no more than 0.0063% by weight of Fe, Si, Mn, Co, Ni, Cu, Zr, Y, Sc or rare earths having the ordinal numbers 21, 57 to 71 and 89 to 103, Be, Cd, In, Sn and/or Pb as well as P, wherein the matrix of the alloy includes intermetallic phases formed of Mg and Al. The alloy is homogenized by annealing at a temperature between 150° C. and 450° C. The homogenized alloy is formed in the temperature range between 200° C. and 400° C.s.

The previously known tolerance limits for impurities do not take into account that wrought magnesium alloys often times are subjected to a thermomechanical treatment, and more particularly to an extended annealing process, which creates the near-equilibrium structures. The metallic elements bond by way of diffusion and form what are known as intermetallic phases, which have a different electrochemical potential, notably a considerably higher potential, than the magnesium matrix, and therefore these intermetallic phases act as cathodes and can trigger galvanic corrosion processes.

The applicant has found that a corrosion-stable alloy matrix can be achieved when complying with the following tolerance limits of individual impurities in % by weight:

Fe, Si, Mn, Co, Ni, Cu each with <0.0005; Zr, Y each with <0.0003; and P<0.0002. Further preferred in this embodiment, the alloy has additional individual impurities in the following tolerance limits (% by weight): Sc or rare earths having the ordinal numbers 21, 57 to 71 and 89 to 103 in total<0.001; Be, Cd, In, Sn and/or Pb each with <0.0003.

Preferably, the corrosion-staple alloy matrix contains impurities in a total amount of no more than 0.0053 Gew. %, which can be achieved when complying with the following tolerance limits of individual impurities in % by weight:

Fe, Si, Mn each with <0.0005; Co, Ni, Cu each with <0.0002; Zr, Y each with <0.0003; Sc or rare earths having the ordinal numbers 21, 57 to 71 and 89 to 103 in total<0.001; Be, Cd, In, Sn and/or Pb each with <0.0003; and P<0.0001.

In particular preferred embodiments, the corrosion-staple alloy matrix contains impurities in a total amount of no more than 0.0022 Gew. %, which can be achieved when complying with the following tolerance limits of individual impurities in % by weight:n:

Fe, Si, Mn each with <0.0002; Co, Ni, Cu, Zr, Y each with <0.0001; Sc or rare earths having the ordinal numbers 21, 57 to 71 and 89 to 103 in total<0.0005; Be, Cd, In, Sn and/or Pb each with <0.0001, and P<0.0001.

It is surprising that the addition of manganese as an alloying element, which is customary in the prior art, can be dispensed with when these tolerance limits are adhered. The formation of the ternary intermetallic phase FeMnSi is suppressed, whereby the corrosion resistance of the alloy is improved.

When the impurity elements are combined, this tolerance limit of the sum of impurities of Fe, Si, Mn, Co, Ni and Cu is no more than 0.003% by weight, preferably no more than 0.0021% by weight and in particular preferred no m ore than 0.0009% by weight.

Preferred magnesium alloys according to the present invention can achieve a tensile strength of >275 MPa, and preferably >300 MPa, a yield point of >200 MPa, and preferably >225 MPa, and a yield ratio of <0.8, and preferably <075, wherein the difference between the tensile strength and yield point is >50 MPa, and preferably >100 MPa.

These significantly improved mechanical properties can be attributed to the formation of solid solutions between aluminum and zinc in the alloy matrix as well as to the intermetallic phases of magnesium and aluminum occurring in the matrix. The basis for the increased tensile strength is the interaction of the dislocations with the particles, whereby the dislocation movement is adversely impacted and additional tension is required in order to generate the same plastic deformation as in an undisturbed matrix.

The improved mechanical properties of the novel magnesium alloys assure that the stents, for example cardiovascular stents, are able to withstand the multiaxial permanent load in the implanted state over the entire support period, despite onsetting degradation of the magnesium matrix due to corrosion.

For the mechanical asymmetry, it is particularly important for the magnesium alloy to have a particularly fine microstructure having a grain size of no more than 7.5 µm, preferably <5 µm, and still more preferably <2.5 µm.

A preferred method for producing a magnesium alloy having the improved mechanical and electrochemical properties is also provided by the invention. The method comprises the following steps:
a) generating high-purity magnesium by vacuum distillation;
b) generating a billet of the alloy by synthesis of the magnesium according to step a) with less or equal 4.0% by weight Zn, 2.0 to 10.0% by weight Al, wherein the alloy content of Al in % by weight is greater than or equal to the alloy content of Zn in % by weight, the remainder being magnesium containing impurities, which promote electrochemical potential differences and/or the formation of precipitations and/or intermetallic phases, in a total amount of no more than 0.0063% by weight of Fe, Si, Mn, Co, Ni, Cu, Zr, Y, Sc or rare earths having the ordinal numbers 21, 57 to 71 and 89 to 103, Be, Cd, In, Sn and/or Pb as well as P, wherein the matrix of the alloy is solid solution hardening due to Al and Zn and is also particle hardening due to the intermetallic phases formed of Mg and Al;
c) homogenizing the alloy by annealing at a temperature between 150° C. and 450° C., with a holding period of 4 to 40 hours; and
d) forming the homogenized alloy in the temperature range between 200° C. and 400° C.

Preferably steps c) and d) can be repeated at least once.

After step c) and before step d) an ageing treatment step can be performed. Depending on the alloy composition and/or the amount and/or type of the grains and/or the grain size ageing treatment step can be performed at a temperature between 20° C. and 300° C. with a holding period of 1 h to 168 h. Preferably the ageing treatment can be performed at a temperature between 20° C. and 275° C., still more preferably at a temperature of 150° C. with a holding period of 120 hours.

In a preferred value range steps c) is performed at a temperature between 250° C. and 450° C. and/or step d) is performed at a temperature between 225° C. and 400° C.

Preferably, the magnesium alloy generated by step a) has a content of Zn less or equal 2.0% by weight, in particular preferably less or equal 1.0% by weight and/or a content of Al in the range of 2.0 to 8.0% by weight, preferably 3.0 to 8.0% by weight and still more preferably 3.0 to 6.0% by weight.

Vacuum distillation is preferably used to produce a starting material for a high-purity magnesium-aluminum-zinc alloy having the required threshold values.

The sum of impurities can be selectively adjusted and in % by weight are:
a) for the individual impurities:
Fe, Si, Mn, Co, Ni, Cu each with <0.0005;
Zr, Y each with <0.0003; and
P<0.0002.
Preferably in this embodiment additional individual impurities in the following tolerance limits (% by weight):
Sc or rare earths having the ordinal numbers 21, 57 to 71 and 89 to 103 in total<0.001; Be, Cd, In, Sn and/or Pb each with <0.0003.
aa) for the individual impurities in a preferred total amount of impurities of no more than 0.0053% by weight:
Fe, Si, Mn each with <0.0005;
Co, Ni, Cu each with <0.0002;
Zr, Y each with <0.0003;
Sc or rare earths having the ordinal numbers 21, 57 to 71 and 89 to 103 in total<0.001;
Be, Cd, In, Sn and/or Pb each with <0.0003; and
P<0.0001.
ab) for the individual impurities in a particularly preferred total amount of impurities of no more than 0.0022% by weight:
Fe, Si, Mn each with <0.0002;
Co, Ni, Cu, Zr, Y each with <0.0001;
Sc or rare earths having the ordinal numbers 21, 57 to 71 and 89 to 103 in total<0.0005;
Be, Cd, In, Sn and/or Pb each with <0.0001; and
P<0.0001.
b) for the combination of individual impurities in total:
Fe, Si, Mn, Co, Ni, Cu no more than 0.003, preferably no more than 0.0021% by weight and in particular preferred no m ore than 0.0009% by weight.

It is particularly advantageous that the preferred method only requires a small number of forming steps. Extrusion, equal channel angular extrusion and/or multiple forging can thus preferably be employed, which assure that a substantially homogeneous fine grain of <10 µm is achieved.

The magnesium alloy produced according to the method, which has the above described advantageous composition and structure, in medical technology, can also be used in the production of implants, for example endovascular implants such as stents, for fastening and temporarily fixing tissue implants and tissue transplantations, orthopedic and dental implants, and neuroimplants.

Particular implants of the invention are in the Cardiovascular field, osteosynthesis field or other areas.

Cardiovascular field in the sense of this application includes
the field of diagnostic, prevention and treatment of all diseases of the cardiovascular system, i.e. heart and blood vessel system,
by mean of active and non-active implants used to support vessels, and vein systems
including coronary, cerebral and peripheral vascular implants like stents, valves, closure devices, occluders, clips, coils, staples, implantable regional drug delivery devices,
implantable electrostimulators (like pacemakers and defibrillators), implantable monitoring devices, implantable electrodes,
system for fastening and temporarily fixing tissue implants and tissue transplantations
field also includes any type of stent as mechanical fix or temporary scaffold to support hollow organs and structures including bones, intervertebral disks Osteosynthesis in the sense of this application includes
the field of treatment of fractured bones for internal fixation and stabilization by mechanical devices such as metal plates, pins, rods, wires, screws, clips, nails, staples excluding stent technology Examples of areas out of the osteosynthesis field or the cardiovascular field are:
Devices for the treatment of diseases of the sinews, joints, muscles, cartilages,
oral (including dental) and maxillo facial implants (excl. osteosynthesis means),
esthetic implants,
supporting tools out of the body,
tissue engineering,
soft tissue implants,
devices for wound care, suture material and clamps,
neurosurgery
local drug delivery (excl. cardiovascular, i.e. lever)
renal

Exemplary Embodiment 1

A magnesium alloy is generated which is composed of 2.0% by weight Zn and 6.0% by weight Al, the remainder being Mg, and contains the following individual impurities in % by weight:
Fe: <0.0005; Si: <0.0005; Mn: <0.0005; Co: <0.0002; Ni: <0.0002; Cu<0.0002, wherein the sum of impurities of Fe, Si, Mn, Co, Ni, Cu is no more than 0.0021% by weight and that of Zr is no more than 0.0003% by weight.

The magnesium produced with aid of vacuum distillation is melted with high-purity Al and Zn in a graphite crucible, and the alloy is subjected to homogenizing annealing at a temperature of 360° C. for a duration of 24 hours, and subsequently to multiple extrusion processes at a temperature of 300° C., so as to produce a precision tube for a cardiovascular stent.

The grain size of the microstructure was <5.5 μm, and the particle size of the intermetallic phases dispersedly distributed in the alloy matrix was 0.5 μm.

The magnesium alloy reached a tensile strength of 310 to 320 MPa and proof stress of approximately 250 MPa [sic]. The yield ratio was 0.79 and the mechanical asymmetry was 1.2.

Exemplary Embodiment 2

A magnesium alloy is generated which is composed of 0.25% by weight Zn and 2.50% by weight Al, the remainder being Mg, and contains the following individual impurities in % by weight:
Fe: <0.0005; Si: <0.0005; Mn: <0.0005; Co: <0.0002; Ni: <0.0002; Cu<0.0002, wherein the sum of impurities of Fe, Si, Mn, Co, Ni, Cu is no more than 0.0021% by weight and that of Zr is no more than 0.0003% by weight.

The magnesium produced with aid of vacuum distillation is melted with high-purity Al and Zn in a graphite crucible, and the alloy is subjected to homogenizing annealing at a temperature of 360° C. for a duration of 24 hours, and subsequently to multiple extrusion processes at a temperature of 300° C., so as to produce a precision tube for a cardiovascular stent.

The grain size of the microstructure was <5.5 μm, and the particle size of the intermetallic phases dispersedly distributed in the alloy matrix was 0.5 μm.

The magnesium alloy reached a tensile strength of 310 to 320 MPa and proof stress of approximately 250 MPa [sic]. The yield ratio was 0.79 and the mechanical asymmetry was 1.2.

Exemplary Embodiment 3

A magnesium alloy is generated which is composed of 5.0% by weight Al, the remainder being Mg, and contains the following individual impurities in % by weight:
Fe: <0.0005; Si: <0.0005; Mn: <0.0005; Co: <0.0002; Ni: <0.0002; Cu<0.0002, wherein the sum of impurities of Fe, Si, Mn, Co, Ni, Cu is no more than 0.0021% by weight and that of Zr is no more than 0.0003% by weight.

The magnesium produced with aid of vacuum distillation is melted with high-purity Al in a graphite crucible, and the alloy is subjected to homogenizing annealing at a temperature of 360° C. for a duration of 24 hours, and subsequently to multiple extrusion processes at a temperature of 300° C., so as to produce a precision tube for a cardiovascular stent.

The grain size of the microstructure was <5.5 μm, and the particle size of the intermetallic phases dispersedly distributed in the alloy matrix was 0.5 μm.

The magnesium alloy reached a tensile strength of 310 to 320 MPa and proof stress of approximately 250 MPa [sic]. The yield ratio was 0.79 and the mechanical asymmetry was 1.2.

Exemplary Embodiment 4

A magnesium alloy is generated which is composed of 3% by weight Al, the remainder being Mg, and contains the following individual impurities in % by weight:
Fe: <0.0005; Si: <0.0005; Mn: <0.0005; Co: <0.0002; Ni: <0.0002; Cu<0.0002, wherein the sum of impurities of Fe, Si, Mn, Co, Ni, Cu is no more than 0.0021% by weight and that of Zr is no more than 0.0003% by weight.

The magnesium produced with aid of vacuum distillation is melted with high-purity Al in a graphite crucible, and the alloy is subjected to homogenizing annealing at a temperature of 360° C. for a duration of 24 hours, and subsequently to multiple extrusion processes at a temperature of 300° C., so as to produce a precision tube for a cardiovascular stent.

The grain size of the microstructure was <5.5 μm, and the particle size of the intermetallic phases dispersedly distributed in the alloy matrix was 0.5 μm.

The magnesium alloy reached a tensile strength of 310 to 320 MPa and proof stress of approximately 250 MPa [sic]. The yield ratio was 0.79 and the mechanical asymmetry was 1.2.

Exemplary Embodiment 5

A magnesium alloy is generated which is composed of 0.25% by weight Zn and 2.0% by weight Al, the remainder being Mg, and contains the following individual impurities in % by weight:
Fe: <0.0005; Si: <0.0005; Mn: <0.0005; Co: <0.0002; Ni: <0.0002; Cu<0.0002, wherein the sum of impurities of Fe, Si, Mn, Co, Ni, Cu is no more than 0.0021% by weight and that of Zr is no more than 0.0003% by weight.

The magnesium produced with aid of vacuum distillation is melted with high-purity Al and Zn in a graphite crucible, and the alloy is subjected to homogenizing annealing at a temperature of 360° C. for a duration of 24 hours and thereafter to an ageing treatment at 125° C. for 120 hours.

Subsequently, the material is subjected to multiple extrusion processes at a temperature of 200° C., so as to produce a precision tube for a cardiovascular stent.

Before the final extrusion step is applied another annealing process is performed at 150° C. for 3 hours.

The grain size of the microstructure was <5.5 μm, and the particle size of the intermetallic phases dispersedly distributed in the alloy matrix was 0.5 μm.

The magnesium alloy reached a tensile strength of 320 to 350 MPa and proof stress of approximately 235 MPa. The yield ratio was 0.70 and the mechanical asymmetry was 1.2.

Exemplary Embodiment 6

A magnesium alloy is generated which is composed of 1.5% by weight Zn and 3.0% by weight Al, the remainder being Mg, and contains the following individual impurities in % by weight:

Fe: <0.0005; Si: <0.0005; Mn: <0.0005; Co: <0.0002; Ni: <0.0002; Cu<0.0002, wherein the sum of impurities of Fe, Si, Mn, Co, Ni, Cu is no more than 0.0021% by weight and that of Zr is no more than 0.0003% by weight.

The magnesium produced with aid of vacuum distillation is melted with high-purity Al and Zn in a graphite crucible, and the alloy is subjected to homogenizing annealing at a temperature of 360° C. for a duration of 24 hours and thereafter to an ageing treatment at 150° C. for 120 hours.

Subsequently, the material is subjected to an extrusion process at a temperature of 200° C., so as to produce a rod with 8 mm diameter to produce screws for craniofacial fixations.

The grain size of the microstructure was <3.0 μm, and the particle size of the intermetallic phases dispersedly distributed in the alloy matrix was 0.5 μm.

The magnesium alloy reached a tensile strength of 340 to 360 MPa and proof stress of approximately 250 MPa [sic]. The yield ratio was 0.71 and the mechanical asymmetry was 1.2.

While specific embodiments of the present invention have been shown and described, it should be understood that other modifications, substitutions and alternatives are apparent to one of ordinary skill in the art. Such modifications, substitutions and alternatives can be made without departing from the spirit and scope of the invention, which should be determined from the appended claims.

Various features of the invention are set forth in the appended claims.

The invention claimed is:

1. A method for producing a magnesium alloy having improved mechanical and electrochemical properties, comprising:
    a) vacuum distilling magnesium to produce a purified magnesium starting material;
    b) melting the magnesium starting material with aluminum to generate a billet of the alloy, the billet having 2.0 to 10.0% by weight Al, the remainder being magnesium containing impurities in a total amount of no more than 0.0063% by weight of Fe, Si, Mn, Co, Ni, Cu, Zr, Y, Sc or rare earths having the ordinal numbers 21, 57 to 71 and 89 to 103, Be, Cd, In, Sn and/or Pb as well as P, wherein a matrix of the alloy includes intermetallic phases formed of Mg and Al;
    c) homogenizing the alloy by annealing at a temperature between 150° C. and 450° C.;
    d) forming of the homogenized alloy in the temperature range between 200° C. and 400° C.

2. The method according to claim 1, comprising annealing with a holding period of between 4 to 40 hours.

3. The method according to claim 1, comprising annealing with a holding period sufficient to produce a homogeneous fine grain of <10 μm.

4. The method according to claim 1, comprising annealing with a holding period of at least 3 hours.

5. The method according to claim 1, wherein individual impurities in the total sum of impurities amount to the following in % by weight: Fe, Si, Mn, Ni, Co, Cu each with <0.0005; Zr, Y each with <0.0003; and P<0.0002.

6. The method according to claim 1, wherein Fe, Si, Mn, Co, Ni, and Cu together total no more than 0.003% by weight.

7. The method according to claim 1, wherein the forming process comprises extrusion, equal channel angular extrusion (EACE) and/or a multiple forging process.

8. The method according to claim 1, wherein steps c) and d) are repeated at least once.

9. The method according to claim 1, wherein step c) is performed at a temperature between 250° C. and 450° C. and/or step d) is performed at a temperature between 225° C. and 400° C.

* * * * *